(12) United States Patent
Eguchi et al.

(10) Patent No.: US 12,082,962 B2
(45) Date of Patent: Sep. 10, 2024

(54) RADIOGRAPHY SYSTEM

(71) Applicant: Konica Minolta, Inc., Tokyo (JP)

(72) Inventors: Mao Eguchi, Kokubunji (JP);
Koutarou Kanamori, Hachioji (JP);
Takeshi Saito, Hachioji (JP); Keisuke Koeda, Higashimurayama (JP);
Nobuyuki Miyake, Yokohama (JP);
Yuuichi Maruta, Hino (JP)

(73) Assignee: Konica Minolta, Inc., Tokyo (JP)

( * ) Notice: Subject to any disclaimer, the term of this patent is extended or adjusted under 35 U.S.C. 154(b) by 263 days.

(21) Appl. No.: 17/353,750

(22) Filed: Jun. 21, 2021

(65) Prior Publication Data

US 2022/0000440 A1  Jan. 6, 2022

(30) Foreign Application Priority Data

Jul. 2, 2020 (JP) .................. 2020-114532

(51) Int. Cl.
*A61B 6/00* (2024.01)
*A61B 6/46* (2024.01)
*A61B 6/58* (2024.01)

(52) U.S. Cl.
CPC .............. *A61B 6/462* (2013.01); *A61B 6/464* (2013.01); *A61B 6/585* (2013.01)

(58) Field of Classification Search
None
See application file for complete search history.

(56) References Cited

U.S. PATENT DOCUMENTS

| 2014/0239189 | A1* | 8/2014 | Sakino | H04N 25/63 |
| | | | | 250/394 |
| 2018/0368797 | A1* | 12/2018 | Kuwata | A61B 6/5217 |
| 2019/0282196 | A1* | 9/2019 | Tezuka | G01T 1/175 |

FOREIGN PATENT DOCUMENTS

| JP | 2002-335446 A | 11/2002 |
| JP | 2013-138360 A | 7/2013 |
| JP | 2019-154785 A | 9/2019 |

OTHER PUBLICATIONS

Office Action dated Nov. 21, 2023 for corresponding Japanese Patent Application No. 2020-114532, with English translation.

* cited by examiner

*Primary Examiner* — Hoon K Song
(74) *Attorney, Agent, or Firm* — LUCAS & MERCANTI, LLP

(57) ABSTRACT

A radiography system includes an image former, a first determiner, and an operation controller. The image former performs serial radiography of repeatedly generating a frame that constitutes a video. The first determiner determines whether a next test action is the serial radiography. The operation controller makes the image former begin turning a switch element on/off in a same manner as a manner in the serial radiography before start of the next test action in a case where the first determiner determines that the next test action is the serial radiography.

14 Claims, 11 Drawing Sheets

RADIOGRAPHY SYSTEM

BACKGROUND

1. Technical Field

The present invention relates to a radiography system.

2. Background Art

According to a known technique, a cycle of reset operation of a semiconductor element and a cycle of acquisition operation of offset data, which are performed before and after imaging of radiographic video, are changed depending on situations.

For example, JP 2002-335446A describes an imaging device including a drive. In an operation state related to imaging of a subject, the drive performs control for a region to be imaged at first intervals. In a standby state not related to imaging of the subject, the drive performs control for the region to be imaged at second intervals shorter than the first intervals.

JP 2013-138360A describes an imaging control device. The imaging control device includes means for controlling a repetition cycle of reading such that the cycle is shorter in first initialization drive than in second initialization drive, based on an acquired shooting mode and a state of a sensor. The first initialization drive is drive in transition from a video shooting mode to a still image shooting mode. The second initialization drive is drive in transition from a non-shooting state to the still image shooting mode.

In video shooting (serial radiography), in order to obtain accurate offset data, it is necessary to drive a device for a predetermined time right before actual radiation. The device is driven like it is while the device receives radiation Therefore, in a case where first serial radiography is followed by second serial radiography, a standby time occurs between shooting actions.

However, the imaging device in JP 2002-335446A controls the time intervals to prevent a life of the device from getting shorter and to prevent detection characteristics from changing over the years. It does not consider modes of imaging.

The technology described in JP 2013-138360A controls a cycle in transition to still image shooting. It does not perform such control in transition to video shooting.

Thus, the prior art such as JP 2002-335446A and JP 2013-138360A could not shorten the standby time between shooting actions in the case where first serial radiography is followed by second serial radiography.

SUMMARY OF INVENTION

The present invention was made in view of the above problems. An object of the present invention is to shorten a standby time between shooting actions without degrading quality of video acquired in the next serial radiography in a case where serial radiography is followed by the next serial radiography.

To achieve the abovementioned object, according to an aspect of the present invention, a radiography system includes:
an image former that performs serial radiography of repeatedly generating a frame that constitutes a video;
a first determiner that determines whether a next test action is the serial radiography; and
an operation controller that makes the image former begin turning a switch element on/off in a same manner as a manner in the serial radiography before start of the next test action in a case where the first determiner determines that the next test action is the serial radiography.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention.

DESCRIPTION OF EMBODIMENTS

Hereinafter, embodiments of the present invention will be described with reference to the drawings. However, the scope of the invention is not limited to the disclosed embodiments.

1. First Embodiment

First, a first embodiment of the present invention will be described.

1-1. Radiography System

Figure 1:
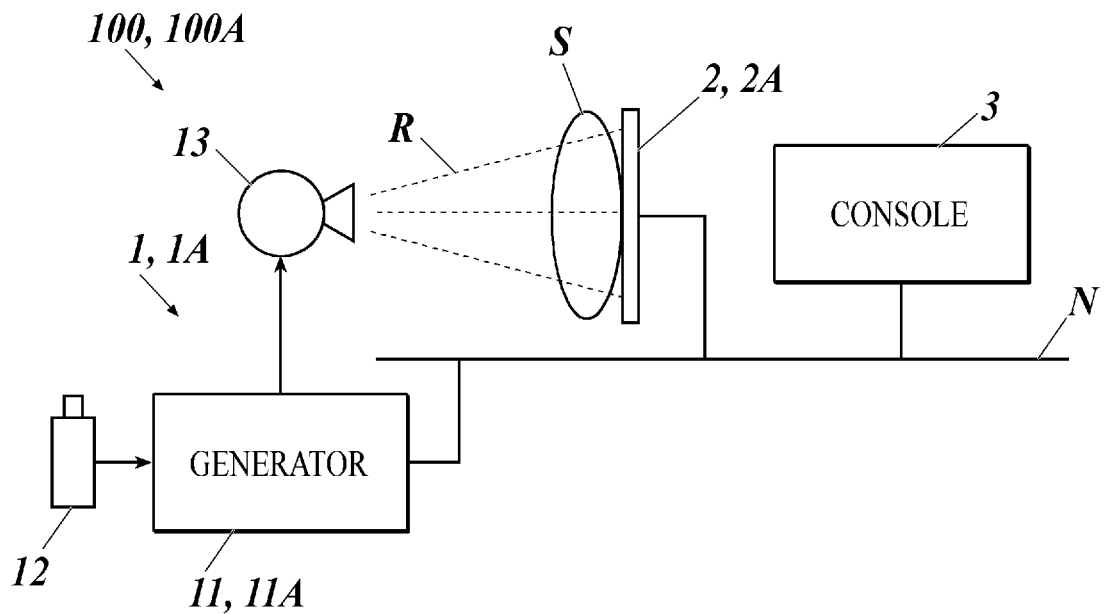
FIG. 1 is a block diagram showing a radiography system according to an embodiment of the present invention.

First, a schematic configuration of a radiography system (hereinafter, system 100) according to the embodiment will be described. FIG. 1 is a block diagram showing the system 100.

Reference numerals in parentheses in FIG. 1 are those in a second embodiment, which will be described later.

As shown in FIG. 1, the system 100 includes a radiation device 1 and a radiation detector 2.

The system 100 according to the embodiment further includes a console 3.

The devices 1 to 3 communicate with each other via, for example, a communication network N (LAN (local area network), WAN (wide area network), the internet, etc.).

The system 100 may communicate with a hospital information system (HIS), a radiology information system (RIS), a picture archiving and communication system (PACS), etc. (not shown).

Radiation Device

The radiation device 1 includes a generator 11, a radiation command switch 12, and a radiation source 13.

The radiation device 1 may be installed in a radiography room, or may be a movable device called a radiation vehicle.

The generator 11 applies a voltage corresponding to preset shooting conditions to the radiation source 13 (tube) in response to operation on the radiation command switch 12.

The shooting conditions includes:
conditions related to a subject S, such as a part to be imaged, a shooting direction, and build; and
conditions related to radiation R such as a tube voltage, a tube current, a radiation time, a current-time product (mAs value), and a frame rate.

The generator 11 repeatedly outputs a first timing signal to the radiation detector 2 at a set cycle.

Details of the generator 11 will be described later.

When the generator 11 applies a voltage to the radiation source 13, the radiation source 13 generates radiation R (for example, X-rays) of a dose corresponding to the applied voltage.

The radiation device 1 having such configuration generates radiation R in a manner corresponding to the set shooting conditions in response to, for example, operation on the radiation command switch 12.

For example, in a case where a set shooting manner is shooting of a still image (hereinafter referred to as still image shooting), the radiation device 1 generates a predetermined dose of radiation for a predetermined time just once.

On the other hand, in a case where the set shooting manner is shooting of video consisting of frames (hereinafter referred to as serial radiography), the radiation device 1 repeatedly generates a predetermined dose of pulsed radiation a predetermined number of times at a set frame rate. The pulsed radiation has a width shorter than that in the still image shooting.

Radiation Detector

The radiation detector 2 generates a radiographic image in response to, for example, operation on the radiation command switch 12, reception of radiation from the radiation device 1, and the like.

For example, in the case where the set shooting manner is the still image shooting, the radiation detector 2 generates a radiographic image just once.

On the other hand, in the case where the set shooting manner is serial radiography, the radiation detector 2 accumulates and releases charges and reads a signal value multiple times in a short time (for example, fifteen times per second) in synchronization with emission of radiation R from the radiation device 1 (i.e., at the set frame rate). Thereby, the radiation detector 2 repeatedly generates a frame that constitutes a video.

Details of the radiation detector 2 will be described later.

Console

The console 3 is constituted by a computer, a dedicated device, and the like.

The console 3 sets various shooting conditions on at least one of the radiation device 1 and the radiation detector 2 based on operation performed by a user, shooting order information acquired from other systems such as HIS and RIS, etc.

Details of the console 3 will be described later.

1-2. Generator

Next, specific configuration of the generator 11 in the system 100 will be described.

Figure 2:
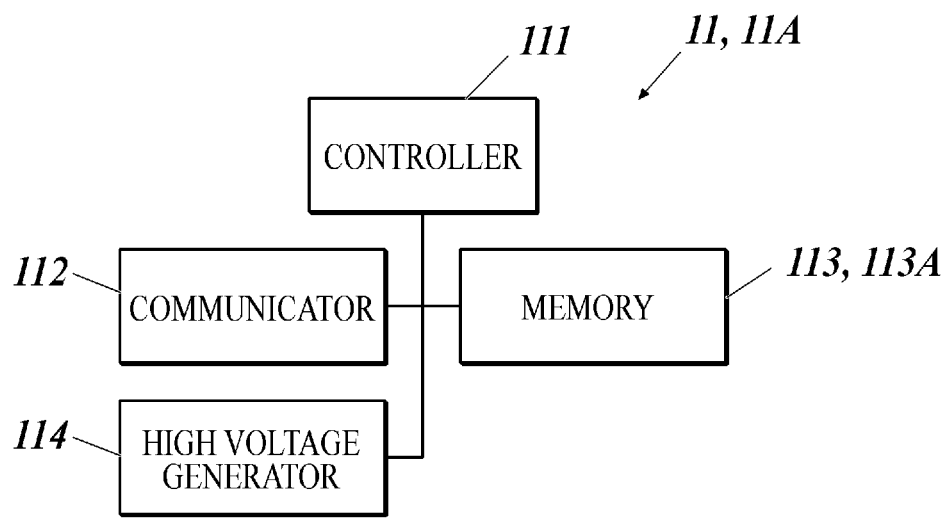
FIG. 2 is a block diagram showing a generator in the radiography system in FIG. 1.
Figure 3:
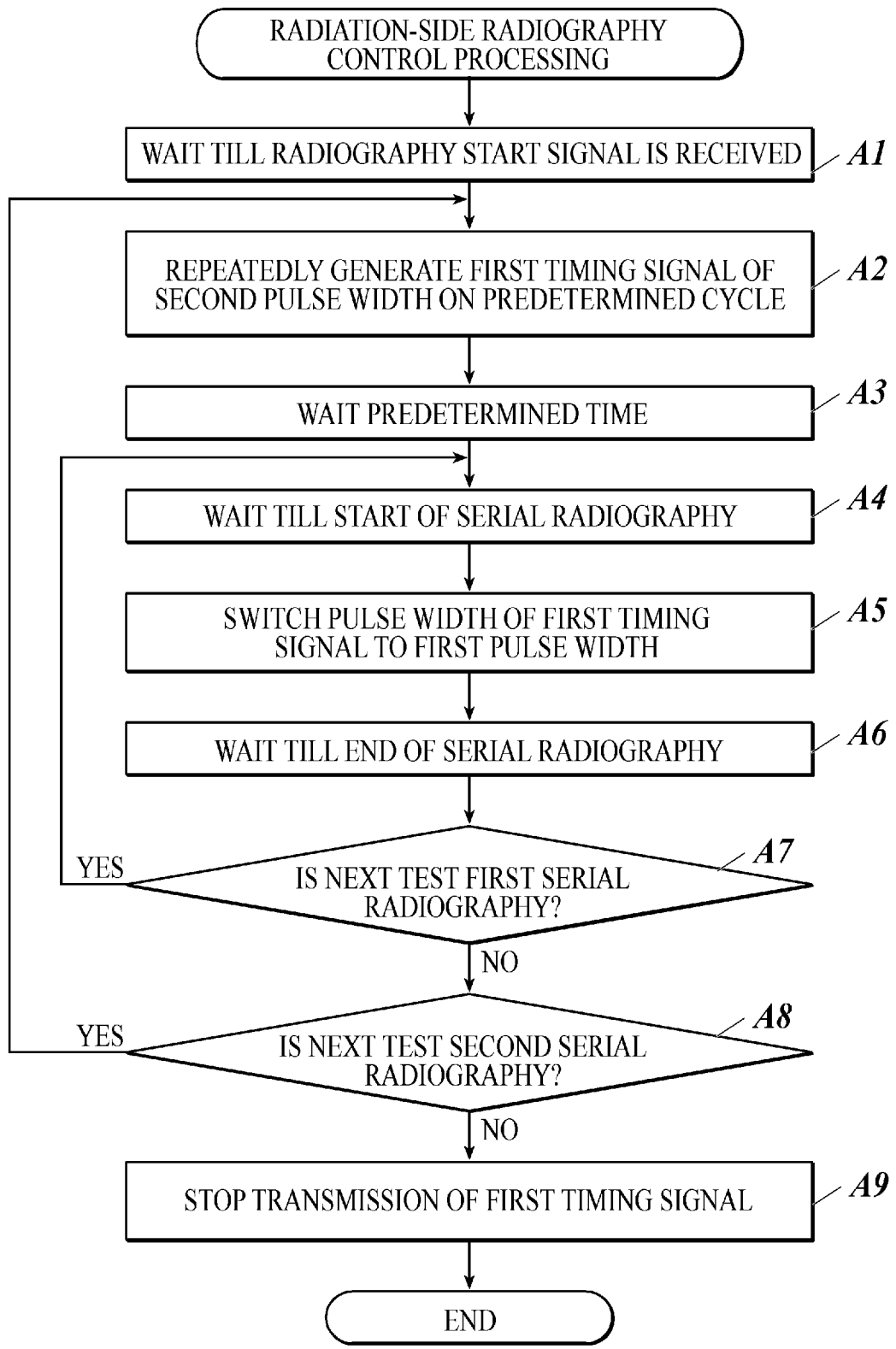
FIG. 3 is a flowchart showing a flow of radiation-side radiography control processing executed by the generator according to a first embodiment.

FIG. 2 is a block diagram showing the generator 11. FIG. 3 is a flowchart showing a flow of the radiation-side radiography control processing executed by the generator 11.

Reference numerals in parentheses in FIG. 2 are those in the second embodiment, which will be described later.

Configuration of Generator

As shown in FIG. 2, the generator 11 includes a radiation-side controller 111, a radiation-side communicator 112, radiation-side memory 113, and a high voltage generator 114.

These parts 111-114 are electrically connected via a bus or the like.

The radiation-side controller 111 is constituted by a CPU (central processing unit), RAM (random access memory), and the like.

The CPU of the radiation-side controller 111 reads various programs stored in the radiation-side memory 113 and develops the programs in the RAM. The CPU executes processing of various kinds according to the developed programs, and comprehensively controls operation of parts of the generator 11.

The radiation-side communicator 112 is constituted by a communication module or the like.

The radiation-side communicator 112 transmits and receives various signals and various data to and from other devices, such as the radiation detector 2 and the console 3, connected via the communication network N.

The storage 113 is constituted by non-volatile semiconductor memory, a hard disk or the like.

The radiation-side memory 113 stores various programs, such as radiation-side radiography control processing described later, executed by the radiation-side controller 111, parameters necessary for executing the programs, and the like.

Every time the high voltage generator 114 receives a radiation timing signal from the generator 11, the high voltage generator 114 applies a high voltage required for generating radiation to the radiation source 13.

Operation of Generator

When predetermined conditions are met, the radiation-side controller 111 of the generator 11 having the above configuration executes the radiation-side radiography control processing, such as the one in FIG. 3.

The predetermined conditions include, for example:
turning-on of the generator 11; and
reception of a predetermined control signal from the radiation detector 2 or the console 3.

In the radiation-side radiography control processing, the radiation-side controller 111 first waits until it receives a radiography start signal from the console 3 (Step A1).

During this standby time, the radiation-side controller 111 receives shooting conditions for the next shooting from the console 3 via the radiation-side communicator 112. The radiation-side controller 111 sets the shooting conditions.

After the radiation-side controller 111 receives the radiography start signal from the console 3, the radiation-side controller 111 repeatedly generates the first timing signal at the set cycle (Step A2).

The radiation-side controller 111 according to the embodiment repeatedly transmits the first timing signal to the radiation detector 2.

The radiation-side controller 111 according to the embodiment transmits the radiation timing signal to the high voltage generator 114 at the same cycle as that for the first timing signal.

The radiation-side controller 111 generates the first timing signal of two types at the same timings. The first type is generated when the radiation-side controller 111 orders radiation while the second type is generated when the radiation-side controller 111 does not order radiation.

In a case where the radiation-side controller 111 according to the embodiment orders radiation, that is, where the radiation command switch 12 is operated, the radiation-side controller 111 generates the first timing signal of the first type having a first pulse width. In a case where the radiation-side controller 111 does not order radiation, that is, where the radiation command switch 12 is not operated, the radiation-side controller 111 generates the first timing signal of the second type having a second pulse width which is different from the first pulse width.

The radiation command switch 12 is not operated right after the radiation-side controller 111 starts transmitting the first timing signal. Therefore, the radiation-side controller 111 transmits the first timing signal of the second pulse width.

The two types of the first timing signal, which consists of the first type for ordering radiation and the second type for not ordering radiation, are different in, for example, intensity of the signal.

After the radiation-side controller 111 starts to generate the first timing signal, the radiation-side controller 111 waits for a predetermined standby time while continuing to generate the first timing signal (Step A3).

The standby time is a time during which the radiation detector 2 is in a reset mode (until warm-up is completed).

After the standby time, the radiation-side controller 111 waits until a first serial radiography is started while continuing to generate the first timing signal (Step A4).

The radiation-side controller 111 according to the embodiment waits until the radiation command switch 12 is operated.

After the first serial radiography is started (i.e., the radiation command switch 12 is operated), the radiation-side controller 111 switches a pulse width of the first timing signal to the first pulse width (Step A5).

After the serial radiography is started, the radiation-side controller 111 waits until the current first serial radiography is completed while continuing to generate the first timing signal (Step A6).

The radiation-side controller 111 according to the embodiment waits until operation of the radiation command switch 12 ends.

After or during the serial radiography, the radiation-side controller 111 executes first radiation-side determination processing (Step A7).

In the first radiation-side determination processing, the radiation-side controller 111 determines whether the next test action is the first serial radiography.

The first serial radiography is radiography having the same frame rate as that in the last or current radiography. Therefore, additional radiography which is performed after failure in one serial radiography is also included in the first serial radiography.

In the first radiation-side determination processing according to the embodiment, the radiation-side controller 111 determines whether the next test action is the first serial radiography based on contents received from the console 3, such as shooting conditions, additional radiography, test completion, etc.

In the first radiation-side determination processing, in a case where the radiation-side controller 111 determines that the next test action is the first serial radiography (YES in Step A7), the radiation-side controller 111 repeats processing from Step A4.

In the first radiation-side determination processing, in a case where the radiation-side controller 111 determines that the next test action is not the first serial radiography (NO in Step A7), the radiation-side controller 111 executes second radiation-side determination processing (Step A8).

In the second radiation-side determination processing, the radiation-side controller 111 determines whether the next test action is second serial radiography.

The second serial radiography is radiography having a frame rate different from the one in the last or current radiography.

In the second radiation-side determination processing according to the embodiment, the radiation-side controller 111 determines whether the next test action is the first serial radiography based on contents received from the console 3, such as shooting conditions, additional radiography, test completion, etc., like the first radiation-side determination processing.

In the second radiation-side determination processing, in a case where the radiation-side controller 111 determines that the next test action is the second serial radiography (YES in Step A8), the radiation-side controller 111 changes the generation cycle of the first timing signal and repeats processing from Step A2.

On the other hand, in the second radiation-side determination processing, in a case where the radiation-side controller 111 determines that the next test action is not the second serial radiography (NO in Step A8), the next test action is the still image shooting or completion of test. The radiation-side controller 111 stops generation of the first timing signal (Step A9), and ends the radiation-side radiography control processing.

1-3. Radiation Detector

Next, details of the radiation detector 2 in the system 100 will be described.

Figure 4:
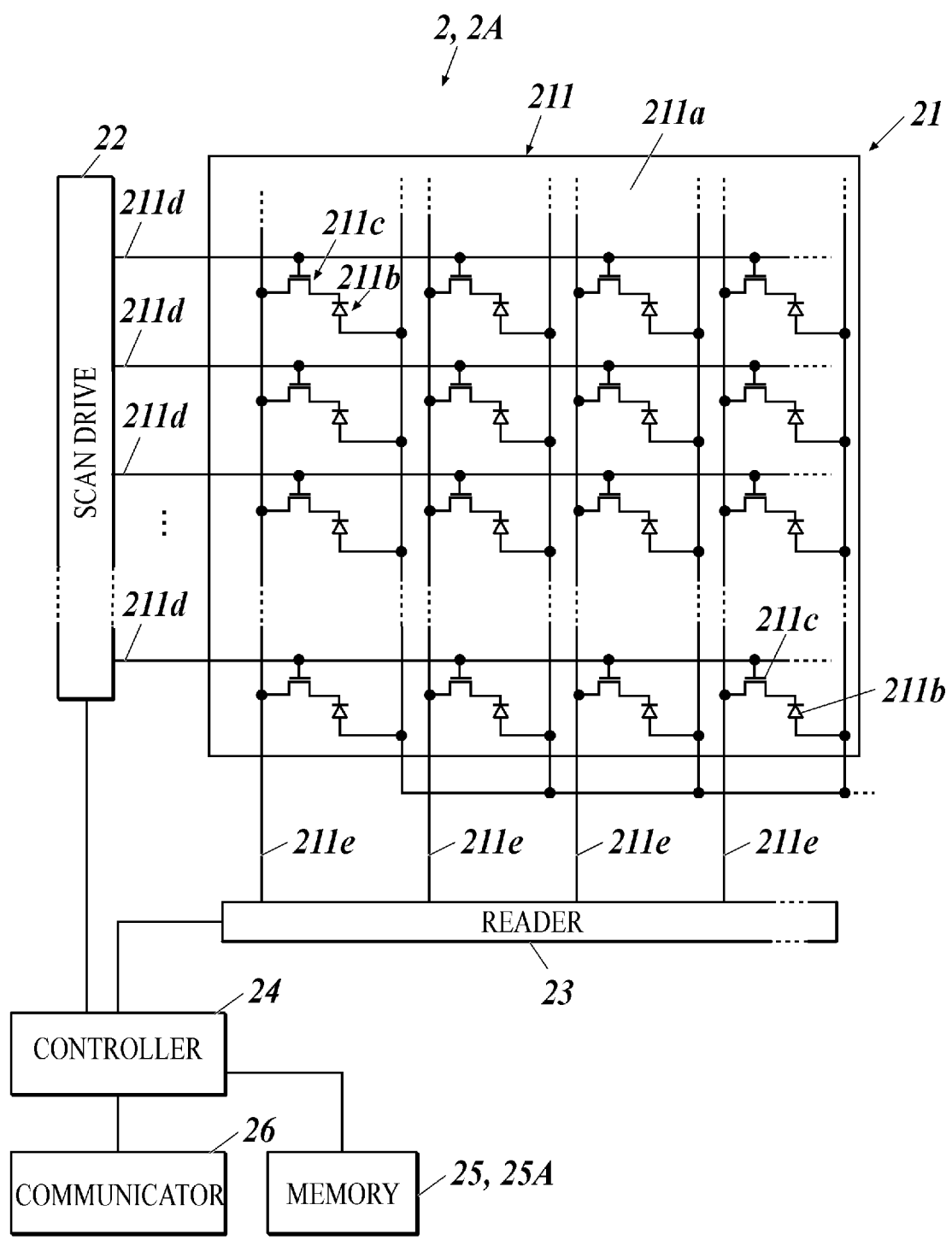
FIG. 4 is a block diagram showing a radiation detector in the radiography system in FIG. 1.
Figure 5:
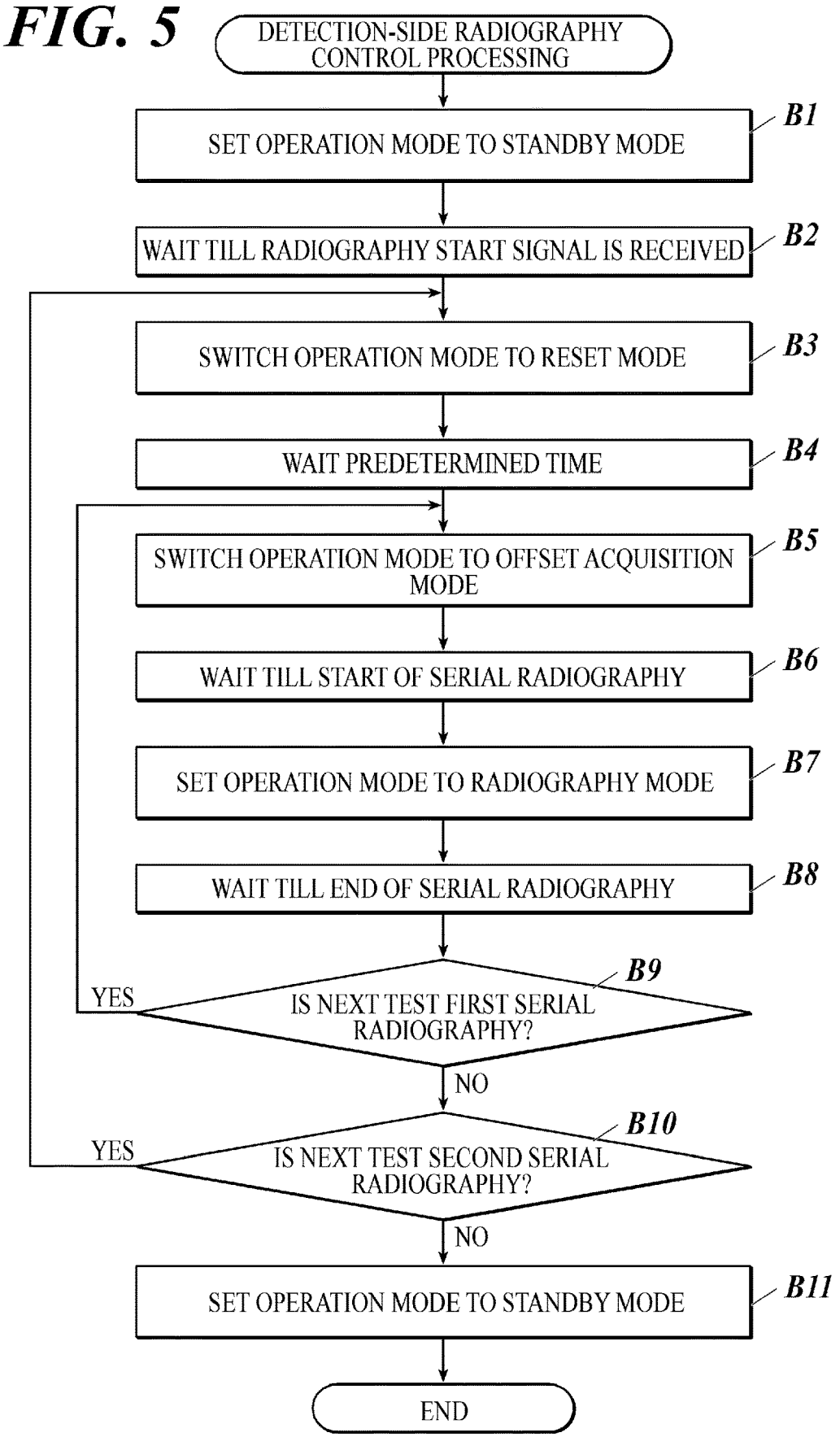
FIG. 5 is a flowchart showing a flow of detection-side radiography control processing executed by the radiation detector according to the first embodiment.

FIG. 4 is a block diagram showing the radiation detector 2. FIG. 5 is a flowchart showing a flow of detection-side radiography control processing executed by the radiation detector 2.

Reference numerals in parentheses in FIG. 4 are those in the second embodiment, which will be described later.

Configuration of Radiation Detector

As shown in FIG. 4, the radiation detector 2 includes a sensor 21, a scan drive 22, a reader 23, a detection-side controller 24, a detection-side memory 25, and a detection-side communicator 26.

The parts 21-26 are electrically connected via a bus or the like.

The sensor 21 includes a scintillator (not shown) and a photoelectric conversion panel 211.

The scintillator is formed in a plate shape with, for example, columnar crystals of CsI.

The scintillator emits electromagnetic waves (for example, visible light) when it receives radiation. A wavelength of the electromagnetic waves is longer than that of radiation. Intensity of electromagnetic waves depends on a dose of received radiation (mAs).

The scintillator is arranged so as to extend parallel to radiation incident surface of a housing (not shown).

The photoelectric conversion panel 211 is arranged so as to extend parallel to the scintillator on an opposite side of a surface of the scintillator facing the radiation incident surface of the housing.

The photoelectric conversion panel 211 includes a substrate 211a, semiconductor elements 211b, and switch elements 211c.

The photoelectric conversion panel 211 according to the embodiment further includes scan lines 211d and signal lines 211e.

The semiconductor element 211b generates an amount of charge suitable for intensity of the electromagnetic wave generated by the scintillator (dose of received radiation).

In the embodiment, the semiconductor elements 211b are placed on a surface of the substrate 211a facing the scintillator. The semiconductor elements 211b are arranged in a two-dimensional shape, such as a matrix shape, corresponding to pixels of a radiographic image.

A power circuit (not shown) applies a bias voltage to the semiconductor elements 211b.

The switch element 211c is provided between each semiconductor element 211b and wiring connected to the reader 23.

Each semiconductor element 211b accumulates and releases an amount of charge corresponding to received radiation in response to turning-on/off of the switch element 211c.

The scan drive 22 constitutes a part of an image former. Each switch element 211c is switched on/off by applying an on-state voltage or an off-state voltage to the scan line 211d of the sensor 21.

The reader 23 constitutes a part of the image former. The reader 23 reads an amount of charge flowing from the semiconductor element 211b via each signal line 211e of the sensor 21 as a signal value.

The reader 23 may perform binning when reading the signal value.

The detection-side controller 24 according to the embodiment is constituted by a CPU (central processing unit), RAM (random access memory), ROM (read only memory), and the like.

Specifically, the CPU of the detection-side controller 24 reads various processing programs stored in the ROM and develops them in the RAM. The CPU executes processing of various kinds according to the developed programs, and comprehensively controls operation of parts of the radiation detector 2.

The detection-side controller 24 generates image data of a radiographic image based on the signal values read by the reader 23.

The detection-side memory 25 according to the embodiment is constituted by volatile memory, such as DRAM (dynamic random access memory).

The detection-side memory 25 stores the image data of the radiographic image generated by the detection-side controller 24.

The detection-side memory 25 may be constituted by non-volatile memory, such as flash memory.

Instead of the ROM of the detection-side controller 24, the detection-side memory 25 may store programs executed by the detection-side controller 24, gate read patterns, pieces of correction data, and the like.

The detection-side memory 25 according to the embodiment serves as a storage that stores a missing map.

The missing map is information (coordinates, etc.) of an abnormal element among the semiconductor elements 211b in the sensor 21. The signal value of the abnormal element which is read by the reader 23 is not within a normal range. The signal value needs to be corrected after shooting.

The detection-side communicator 26 is constituted by a wired communication module, a wireless communication module, and the like. The detection-side communicator 26 transmits and receives various signals and various data, such as radiographic image data, to and from other devices, such as the radiation device 1 and the console 3, connected via the communication network N (LAN (local area network), WAN (wide area network), the internet, etc.) by wire or wirelessly.

Operation of Radiation Detector

When predetermined conditions are met, the detection-side controller 24 of the radiation detector 2 having the above configuration executes the detection-side radiography control processing, such as the one in FIG. 5.

The predetermined conditions include, for example:
turning-on of the radiation detector 2; and
reception of a predetermined control signal from the generator 11 of the radiation device 1 or the console 3.

In the detection-side radiography control processing, the detection-side controller 24 sets operation mode of the scan drive 22 and the reader 23 to a standby mode (Step B1).

In the standby mode, the detection-side controller 24 stops drive of the reader 23 and stops the scan drive 22 from turning on/off the switch element 211c.

After the detection-side controller 24 sets operation mode to the standby mode, the detection-side controller 24 waits until it receives a radiography start signal from the console 3 (Step B2).

After the detection-side controller 24 receives the radiography start signal from the console 3, the detection-side controller 24 switches the operation mode of the scan drive 22 and the reader 23 to a reset mode (Step B3).

In the reset mode, the detection-side controller 24 performs reset operation.

Specifically, the detection-side controller 24 stops drive of the reader 23 and makes the scan drive 22 turn the switch element 211c on/off.

The detection-side controller 24 performs the reset operation every time the first timing signal is received from the generator 11 of the radiation device 1.

Since serial radiography has not begun at this stage, the detection-side controller 24 repeats the reset operation before serial radiography.

After the detection-side controller 24 switches the operation mode to the reset mode, the detection-side controller 24 waits for a standby time (Step B4).

During the standby time, the switch element 211c is repeatedly turned on/off, and the radiation detector 2 is warmed up.

The standby time after switching to the reset mode, the detection-side controller 24 switches the operation mode of the scan drive 22 and the reader 23 to an offset acquisition mode (Step B5).

In the offset acquisition mode, the detection-side controller 24 drives the reader 23 like it does when frames are generated. Further, the detection-side controller 24 makes the scan drive 22 turn the switch element 211c on/off.

Every time the detection-side controller 24 receives the first timing signal from the generator 11 of the radiation device 1, the detection-side controller 24 drives the reader 23 and turns the switch element 211c on/off.

As a result, offset data is repeatedly generated at the same cycle as that of the first timing signal.

After the detection-side controller 24 switches the operation mode to the offset acquisition mode, the detection-side controller 24 waits until serial radiography begins (Step B6).

The detection-side controller 24 according to the embodiment repeatedly determines whether a pulse width of the first timing signal received from the generator 11 of the radiation device 1 is the same as the first pulse width until the pulse width reaches the first pulse width, which is a pulse width in the case where the first timing signal orders radiation.

After serial radiography begins, the detection-side controller 24 switches the operation mode of the scan drive 22 and the reader 23 to the shooting mode (Step B7).

In the shooting mode, the detection-side controller 24 drives the scan drive 22 and the reader 23 like it does in the offset acquisition mode.

While the switch element 211*c* is off, a frame is repeatedly generated by receiving radiation from the radiation device 1.

The detection-side controller 24 waits until the current first serial radiography is completed while continuing to generate the first timing signal (Step B8).

The radiation-side controller 111 according to the embodiment repeatedly determines whether a pulse width of the first timing signal received from the generator 11 of the radiation device 1 is the same as the second pulse width until the pulse width reaches the second pulse width.

After or during serial radiography, the detection-side controller 24 executes a first determination processing (Step B9).

In the first determination processing, the detection-side controller 24 determines whether the next test action is the first serial radiography.

In the first determination processing, in a case where the detection-side controller 24 determines that the next test action is the first serial radiography (YES in Step B9), the detection-side controller 24 repeats processing from Step B5.

Thus, even when the first serial radiography is completed and the detection-side controller 24 determines that a pulse width of the first timing signal has changed from the first pulse width, which is the pulse width of the first timing signal ordering radiation, to the second pulse width, which is the pulse width of the first timing signal not ordering radiation, the detection-side controller 24 changes operation mode of the scan drive 22 and the reader 23 not to the standby mode but to a shorter standby time mode.

In the first detection-side determination processing, in a case where the detection-side controller 24 determines that the next test action is not the first serial radiography (NO in Step B9), the detection-side controller 24 executes a second detection-side determination processing (Step B10).

In the second detection-side determination processing, the detection-side controller 24 determines whether the next test action is the second serial radiography.

In the second detection-side determination processing, in a case where the detection-side controller 24 determines that the next test action is the second serial radiography (YES in Step B10), the detection-side controller 24 changes a setting of frame rate and repeats processing from Step B3.

On the other hand, in the second detection-side determination processing, in a case where the detection-side controller 24 determines that the next test action is not the second serial radiography (NO in Step B10), the next test action is shooting of a still image or completion of test. The detection-side controller 24 switches the operation mode of the scan drive 22 and the reader 23 to the standby mode (Step B11), and ends the detection-side radiography control processing.

The detection-side controller 24 serves as a first determiner by executing the detection-side determination processing described above.

The detection-side controller 24 also serves as a third determiner by determining the pulse width.

The detection-side controller 24 further serves as an operation controller by switching the operation mode.

In the detection-side radiography control processing, the detection-side controller 24 may execute a second determination processing of determining whether a cable is connected to the radiation detector 2 in the next test action.

In a case where the detection-side controller 24 determines that the cable is not connected to the radiation detector 2 in the next operation, the detection-side controller 24 may change the operation mode of the scan drive 22 and the reader 23 to the standby mode whatever the determination result in the first determination processing is.

In that case, the radiation-side controller 111 serves as a second determiner. Power is saved while the cable is not connected, that is, while power cannot be supplied from other devices.

The radiation detector 2 may include a measurer (thermometer or the like) that measures a temperature of the reader 23.

In a case where a temperature of the radiation detector 2 exceeds a predetermined threshold value, the detection-side controller 24 may acquire a missing map based on pieces of offset data which are acquired while the operation mode is the offset acquisition mode. The missing map corresponds to the temperature measured by the measurer. The detection-side controller 24 replaces a missing map stored in the detection-side memory 25 with the acquired missing map.

A signal value outputted from the semiconductor element 211*b* varies depending on temperature and sometimes goes out of a normal range. However, the detection-side controller 24 serves as an acquisition unit and an update unit so that generated frames are accurately corrected however the temperature is.

The detection-side controller 24 may set the standby time suitable for a part to be imaged next.

In that case, the detection-side controller 24 serves as a time setting unit. It prevents video quality from varying depending on parts to be imaged.

In a case where the detection-side controller 24 determines that the next test action is the first serial radiography or the second serial radiography, the detection-side controller 24 may notify a notification unit of how long the standby time before start of the next serial radiography is.

The notification unit includes, for example, a display that displays numbers and a speaker that outputs voice.

The detection-side controller 24 serves as a notification controller. A subject knows how long it takes before the next serial radiography begins.

1-4. Console

Next, details of the console 3 in the system 100 will be described.

Figure 6:
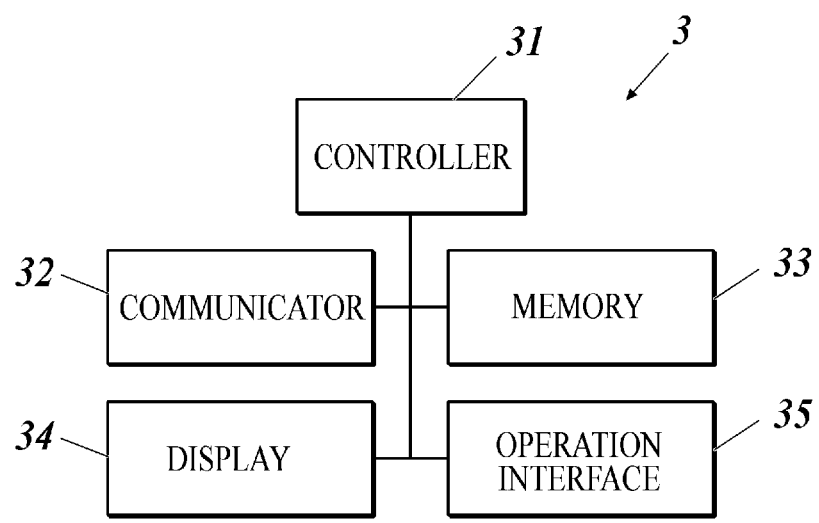
FIG. 6 is a block diagram showing a console in the radiography system in FIG. 1.
Figure 7:
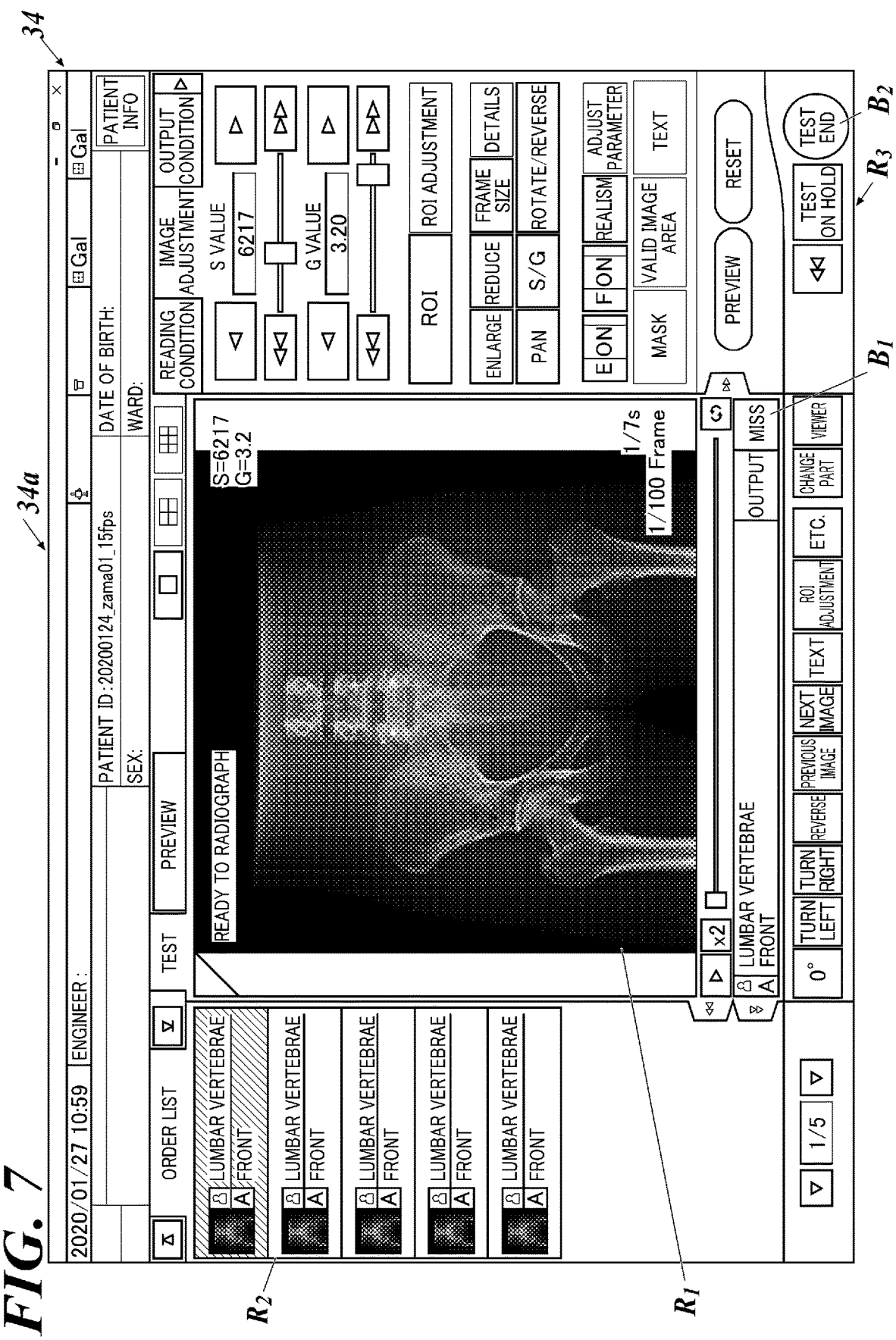
FIG. 7 shows an example of a screen displayed by the console in FIG. 6.

FIG. 6 is a block diagram showing the console 3. FIG. 7 is a diagram showing an example of a screen displayed by the console 3.

Configuration of Console

As shown in FIG. 6, the console 3 includes a controller 31, a communicator 32, a memory 33, a display 34, and an operation interface 35.

The parts 31-34 are electrically connected via a bus or the like.

The controller 31 includes a CPU (central processing unit) and RAM (random access memory) (not shown).

The CPU reads various processing programs stored in the memory 33 and develops them in the RAM.

The CPU executes processing of various kinds according to the processing programs to comprehensively control operation of the parts of the console 3.

The communicator 32 is constituted by a wired communication module, a wireless communication module, and the like. The communicator 32 transmits and receives various signals and various data, such as radiographic image data, to and from other devices, such as the radiation device 1 and the radiation detector 2, connected via the communication network N (LAN (local area network), WAN (wide area network), the internet, etc.) by wire or wirelessly.

The storage 32 is constituted by non-volatile semiconductor memory, a hard disk, or the like.

The memory 33 stores various programs executed by the controller 31, parameters necessary for executing the programs, and the like.

The display 34 displays various screens used by a user for diagnosis.

The display 34 is constituted by, for example, an LCD (liquid crystal display), an ELD (electronic luminescent display), a CRT (cathode ray tube), or the like.

The display 34 displays radiographic images or the like corresponding to image signals received from the controller 31.

The operation interface 35 is an operation unit operated by a user.

The operation interface 35 includes a keyboard having cursor keys, number keys, and various function keys, a pointing device such as a mouse, and a touch panel piled on a surface of the display 34.

The operation interface 35 outputs control signals corresponding to user's operation to the controller 31.

Operation of Console

The controller 31 of the console 3 having such configuration displays, for example, a confirmation screen 34a in FIG. 7.

The confirmation screen 34a includes an image display area $R_1$, an order display area $R_2$, and a button display area $R_3$.

The image display region $R_1$ is an area where a video generated by the radiation detector 2 or a preview video obtained by processing data of the video is displayed.

The order display area $R_2$ is an area where a list of order information for radiography to be performed is displayed.

As shooting conditions for the next radiography, the controller 31 transmits shooting conditions corresponding to a display field displayed at the top to the generator 11 of the radiation device 1 and the radiation detector 2, respectively.

In a case where a display field of one order information in the list is operated, the controller 31 may transmit shooting conditions corresponding to the operated display field as shooting conditions for the next shooting.

The button display area $R_3$ is an area where various operation buttons are displayed.

The operation buttons include a miss button $B_1$ and a test end button B2.

A user watches a video or a preview video displayed on the image display region $R_1$. In a case where the user determines that the video includes a problem, the user operates the miss button $B_1$.

If the miss button $B_1$ is operated, the controller 31 transmits an order of re-radiography to the generator 11 and the radiation detector 2.

The test end button B2 is a button operated by a user to end a test.

If the test end button B2 is operated, the controller 31 transmits an order to end radiography to the generator 11 and the radiation detector 2.

1-5. Operation of System

Next, detailed operation of the system 100 will be described.

Figure 8:
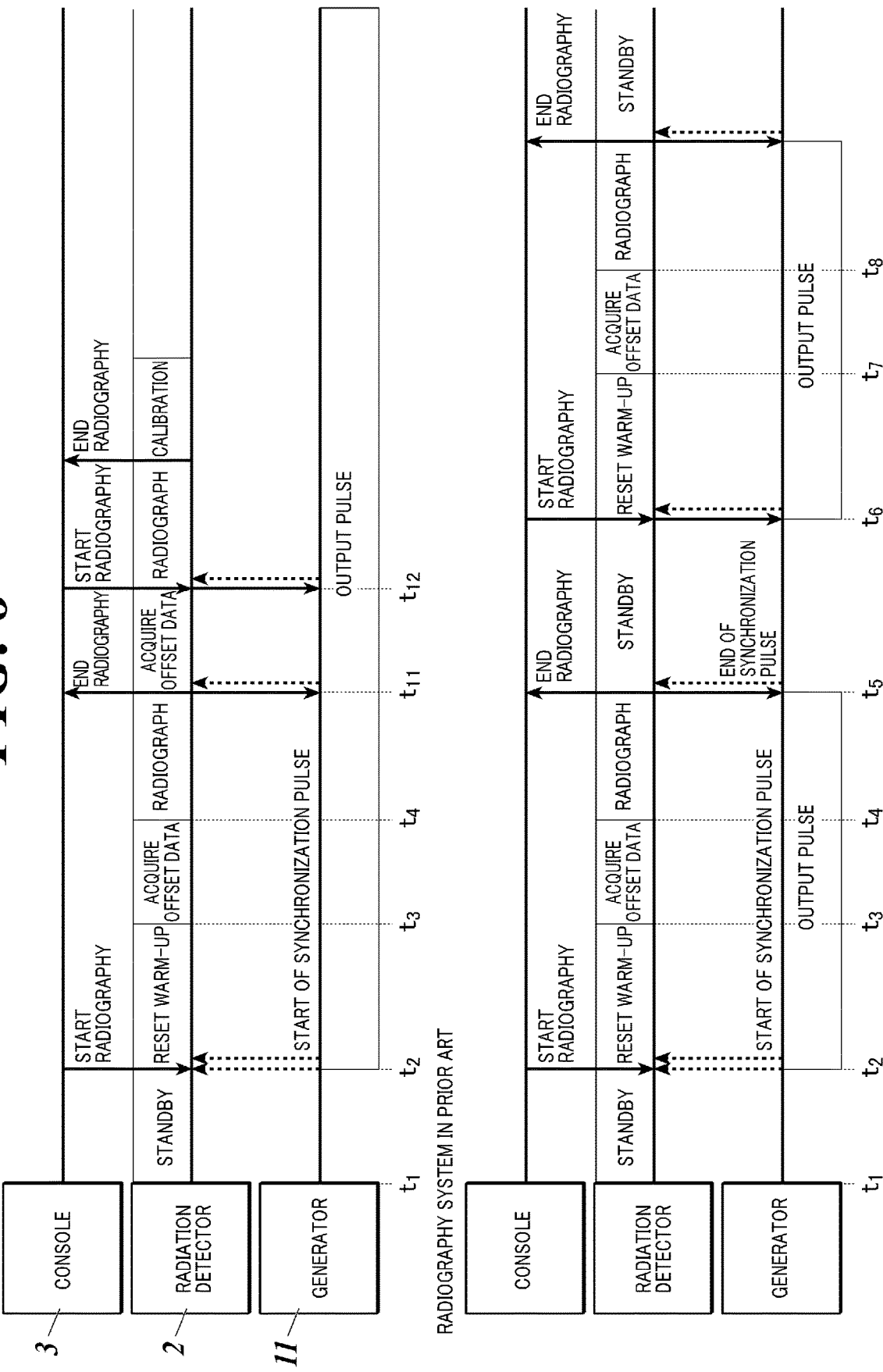
FIG. 8 is a timing chart showing operation of the radiography system according to the first embodiment.

FIG. 8 is a timing chart showing operation of the system 100 and operation of a conventional radiography system.

As shown in the upper part of FIG. 8, when the system 100 is turned on, an operation mode of the radiation detector 2 enters the standby mode ($t_1$).

The console 3 transmits a radiography start signal to the generator 11 of the radiation device 1 and the radiation detector 2 ($t_2$).

After the generator 11 receives the radiography start signal, the generator 11 generates the first timing signal. On the other hand, the radiation detector 2 switches the operation mode to the reset mode.

A standby time after switching to the reset mode, the radiation detector 2 switches the operation mode to the offset acquisition mode ($t_3$).

In the offset acquisition mode, when the radiation command switch 12 of the radiation device 1 is operated, the generator 11 switches the pulse width of the first timing signal to the first pulse width. On the other hand, the radiation detector 2 switches the operation mode to the shooting mode ($t_4$). Thereby serial radiography is performed.

In a case where the next test action is the first serial radiography, the generator 11 switches the pulse width of the first timing signal to the second pulse width after current serial radiography. On the other hand, the radiation detector 2 switches the operation mode to the offset acquisition mode ($t_{11}$).

In the offset acquisition mode, when the radiation command switch 12 of the radiation device 1 is operated, the generator 11 switches the pulse width of the first timing signal to the first pulse width. On the other hand, the radiation detector 2 switches the operation mode to the shooting mode ($t_{12}$). Thereby the next serial radiography is performed.

In the conventional radiography system, as shown in the lower part of FIG. 8, in the case where the next test action is the first serial radiography, a generator stops output of a timing signal after current serial radiography. On the other hand, a radiation detector switches an operation mode to the standby mode ($t_5$).

A console sends a radiography start signal to the generator and the radiation detector ($t_6$).

When the generator receives the radiography start signal, it generates the timing signal. The radiation detector 2 switches the operation mode to the reset mode.

A standby time after switching to the reset mode, the radiation detector switches the operation mode to the offset acquisition mode ($t_7$). At this time, the console 3 displays a phrase "ready to radiograph" on a display screen 34a.

In the offset acquisition mode, when a radiation command switch is operated, serial radiography is performed ($t_8$).

As described above, according to the conventional radiography system, it is necessary to go through the standby mode, the reset mode, and the offset acquisition mode between end of serial radiography and start of the next serial radiography. However, the system 100 switches the operation mode to the offset acquisition mode after serial radiography ($t_{11}$). As soon as the radiation command switch 12 is operated, the next serial radiography begins.

The standby time before the next shooting is shortened by a difference between:

a time between $t_5$ and $t_6$; and a time between $t_{11}$ and $t_{12}$ in FIG. 8.

Figure 9:
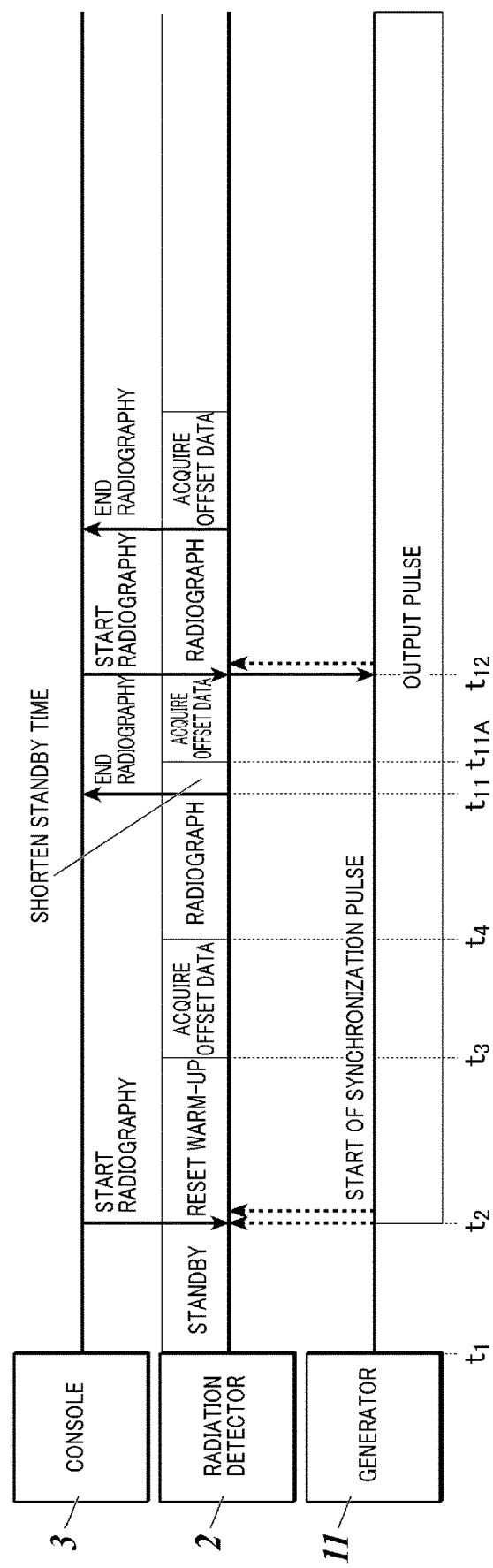
FIG. 9 is a timing chart showing operation of the radiography system according to a modification of the first embodiment.

As shown in FIG. 9, the system 100 may switch the operation mode of the radiation detector 2 to the shorter standby time mode (reset mode) after serial radiography ($t_{11}$). The system 100 switches the operation mode to the offset acquisition mode a predetermined standby time after switching to the shorter standby time mode ($t_{11A}$).

1-6. Advantageous Effect

As described above, after or during serial radiography by the radiation detector 2, the system 100 according to the embodiment determines that the next test action is the first serial radiography which has the same frame rate as that in the last or current radiography. Then, before the next test action begins, the system 100 makes the radiation detector 2 turn the switch element on/off like it does in serial radiography (the system 100 switches the operation mode to the offset acquisition mode).

According to the system 100, when serial radiography is followed by the next serial radiography, the standby time between shooting actions is shortened without degrading quality of video acquired in the next serial radiography.

In a case where additional radiography is performed after failure in one serial radiography, a length of the standby time is not so long as that in a case where serial radiography is newly performed.

2. Second Embodiment

Next, a second embodiment of the present invention will be described.

The same reference numerals are given to the same configurations as those in the first embodiment, and the description thereof are omitted.

2-1. Radiography System

First, difference between the radiography system according to the second embodiment (hereinafter, system 100A) and the system 100 according to the first embodiment will be explained.

As shown in FIG. 1, the system 100A includes a radiation device 1A and a radiation detector 2A in addition to a console 3 like the one in the first embodiment.

2-2. Generator

Next, difference between a generator 11A in the system 100A and the generator 11 according to the first embodiment will be described.

Figure 10:
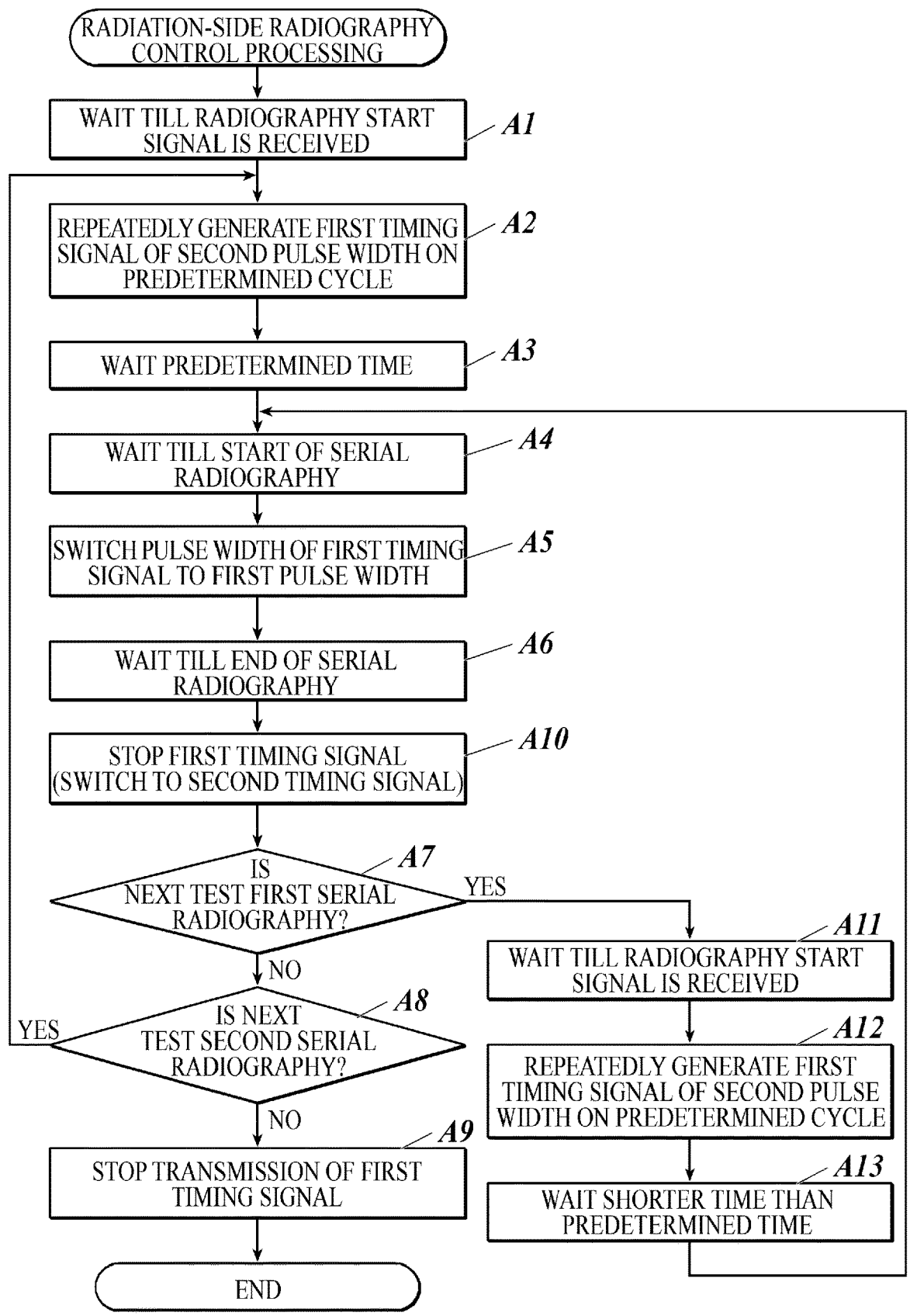
FIG. 10 is a flowchart showing a flow of the radiation-side radiography control processing executed by the generator according to the second embodiment.

FIG. 10 is a flowchart showing a flow of the radiation-side radiography control processing by the generator 11A.

As shown in FIG. 2, the generator 11A includes an radiation-side memory 113A in addition to a radiation-side controller 111, a radiation-side communicator 112, and a high voltage generator 114 like those in the generator 11 according to the first embodiment.

The radiation-side storage 113A is constituted by non-volatile semiconductor memory, a hard disk or the like.

The radiation-side memory 113A stores various programs, such as radiation-side radiography control processing described later, executed by the radiation-side controller 111, parameters necessary for executing the programs, and the like.

When predetermined conditions are met, the radiation-side controller 111 of the generator 11A having such configuration executes the radiation-side radiography control processing, such as the one in FIG. 10.

In this radiation-side radiography control processing, the radiation-side controller 111 first executes processing of Steps A1-A6 like the first embodiment.

After serial radiography, the radiation-side controller 111 transmits an order to generate the second timing signal to the radiation detector 2 and stops the first timing signal (Step A10).

After stopping the first timing signal, the radiation-side controller 111 executes the first radiation-side determination processing (Step A7).

In the first radiation-side determination processing, in a case where the radiation-side controller 111 determines that the next test action is not the first serial radiography (NO in Step A7), the radiation-side controller 111 executes processing from Step A8 like the first embodiment.

On the other hand, in the first radiation-side determination processing, in a case where the radiation-side controller 111 determines that the next test action is the first serial radiography (YES in Step A7), the radiation-side controller 111 waits until it receives the radiography start signal from the console 3 (Step A11).

After the radiation-side controller 111 receives the radiography start signal from the console 3, the radiation-side controller 111 transmits an order to stop the second timing signal to the radiation detector 2 and resumes generation of the first timing signal (Step A12).

After the radiation-side controller 111 resumes generation of the first timing signal, the radiation-side controller 111 waits for a time shorter than the standby time in Step A3 while continuing to generate the first timing signal (Step A13). The radiation-side controller 111 repeats processing from Step A4.

The detection-side controller 24 according to the embodiment serves as a first signal generator by repeatedly generating the first timing signal at a set cycle in processing of Step A2 and processing of Step A12.

2-3. Radiation Detector

Next, difference between the radiation detector 2A in the system 100A and the radiation detector 2 according to the first embodiment will be described.

Figure 11:
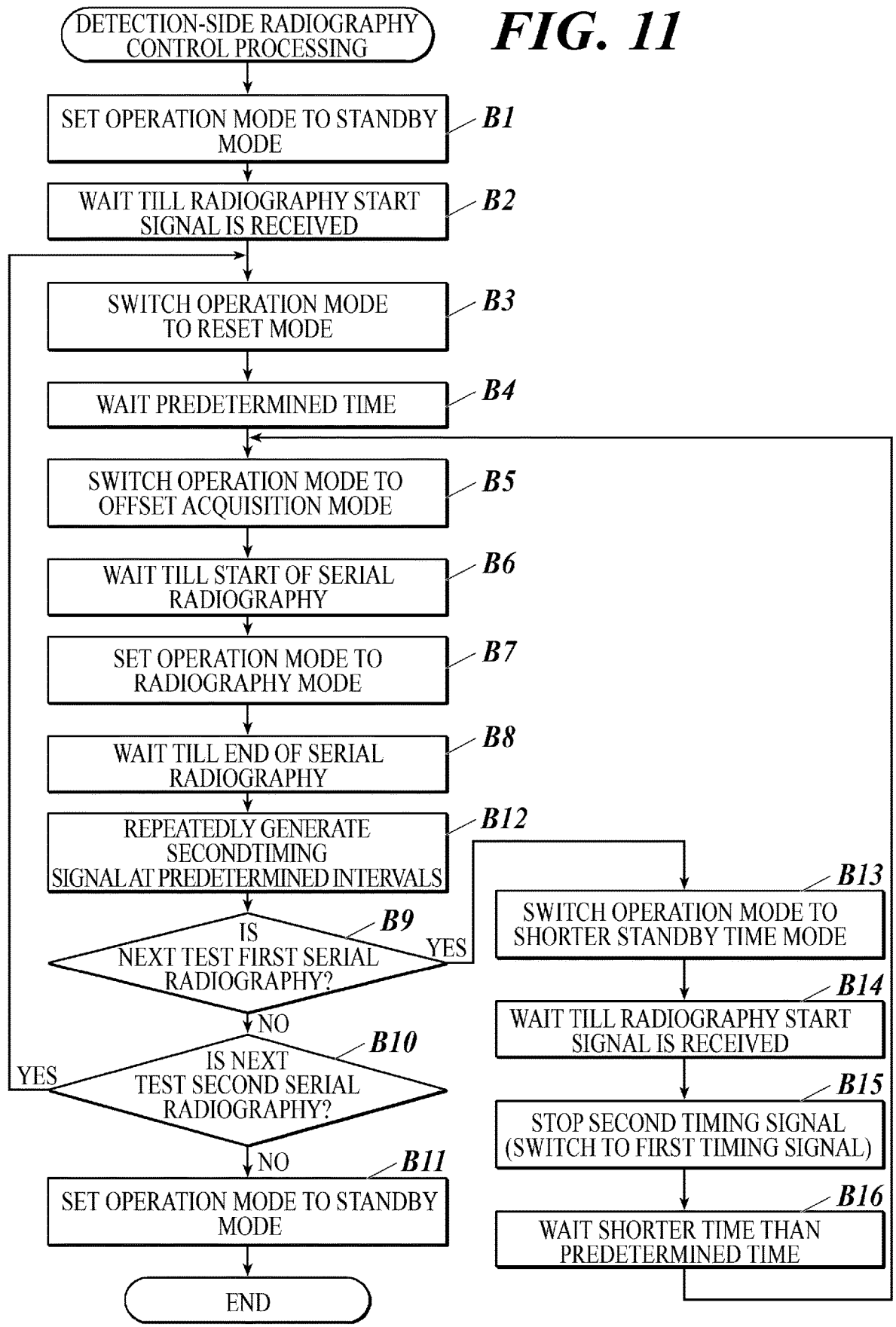
FIG. 11 is a flowchart showing the flow of the detection-side radiography control processing executed by the radiation detector according to the second embodiment.

FIG. 11 is a flowchart showing a flow of the detection-side radiography control processing executed by the radiation detector 2A.

As shown in FIG. 4, the radiation detector 2A includes a detection-side memory 25A in addition to a sensor 21, a scan drive 22, a reader 23, a detection-side controller 24, and a detection-side communicator 26 like those in the radiation detector 2 according to the first embodiment.

The detection-side memory 25A is constituted by non-volatile semiconductor memory, a hard disk, or the like.

The radiation-side memory 25A stores various programs, such as radiation-side radiography control processing described later, executed by the radiation-side controller 24, parameters necessary for executing the programs, and the like.

When predetermined conditions are met, the detection-side controller 24 of the radiation detector 2A having such configuration executes the detection-side radiography control processing, such as the one in FIG. 11.

In the detection-side radiography control processing, the detection-side controller 24 first executes processing of Steps B1-B8 like the first embodiment.

While the detection-side controller 24 executes processing of Steps B1-B8, a generator 11A of the radiation device 1A generates the first timing signal.

While the generator 11A generates the first timing signal, the detection-side controller 24 repeats the reset operation or generation of a frame based on the first timing signal.

After serial radiography, the detection-side controller 24 repeatedly generates the second timing signal at a set cycle (Step B12).

The detection-side controller 24 generates the second timing signal so as to be at the same phase as that of the first timing signal.

The detection-side controller 24 may start generating the second timing signal before end of serial radiography.

The detection-side controller 24 serves as a second signal generator by repeatedly generating the second timing signal at a set cycle.

At the time when processing of Step B12 begins, the generator 11A of the radiation device 1A stops the first timing signal.

While the generator 11A does not generate the first timing signal, the detection-side controller 24 repeats the reset operation based on the second timing signal.

After the generator 11A generates the second timing signal, the detection-side controller 24 executes the first determination processing (Step B9).

In the first detection-side determination processing, in a case where the detection-side controller 24 determines that the next test action is not the first serial radiography (NO in Step B9), the detection-side controller 24 executes processing from Step B10 like the first embodiment.

On the other hand, in a case where the detection-side controller 24 determines that the next test action is the first serial radiography (YES in Step B9), the detection-side controller 24 switches an operation mode of the scan drive 22 and the reader 23 to the shorter standby time mode (Step B13).

In the shorter standby time mode, the detection-side controller 24 operates like it does in the standby mode except that it performs the reset operation.

After the detection-side controller 24 switches the operation mode to the shorter standby time mode, the detection-side controller 24 waits until it receives the radiography start signal from the console 3 (Step B14).

After the detection-side controller 24 receives the radiography start signal from the console 3, the detection-side controller 24 stops the second timing signal (Step B15).

After the detection-side controller 24 stops the second timing signal, the detection-side controller 24 waits for a time shorter than the standby time in Step B4 (Step B16). The detection-side controller 24 repeats processing from Step B5.

In the detection-side radiography control processing, in a case where the second timing signal is stopped and generation of the first timing signal is resumed, the detection-side controller 24 may apply offset correction to a generated frame based on pieces of offset data, the number of pieces corresponding to a level of difference in the phase between the first timing signal and the second timing signal.

2-4. Operation of System

Next, difference between operation of the system 100A and operation of the system 100 according to the first embodiment will be described.

Figure 12:
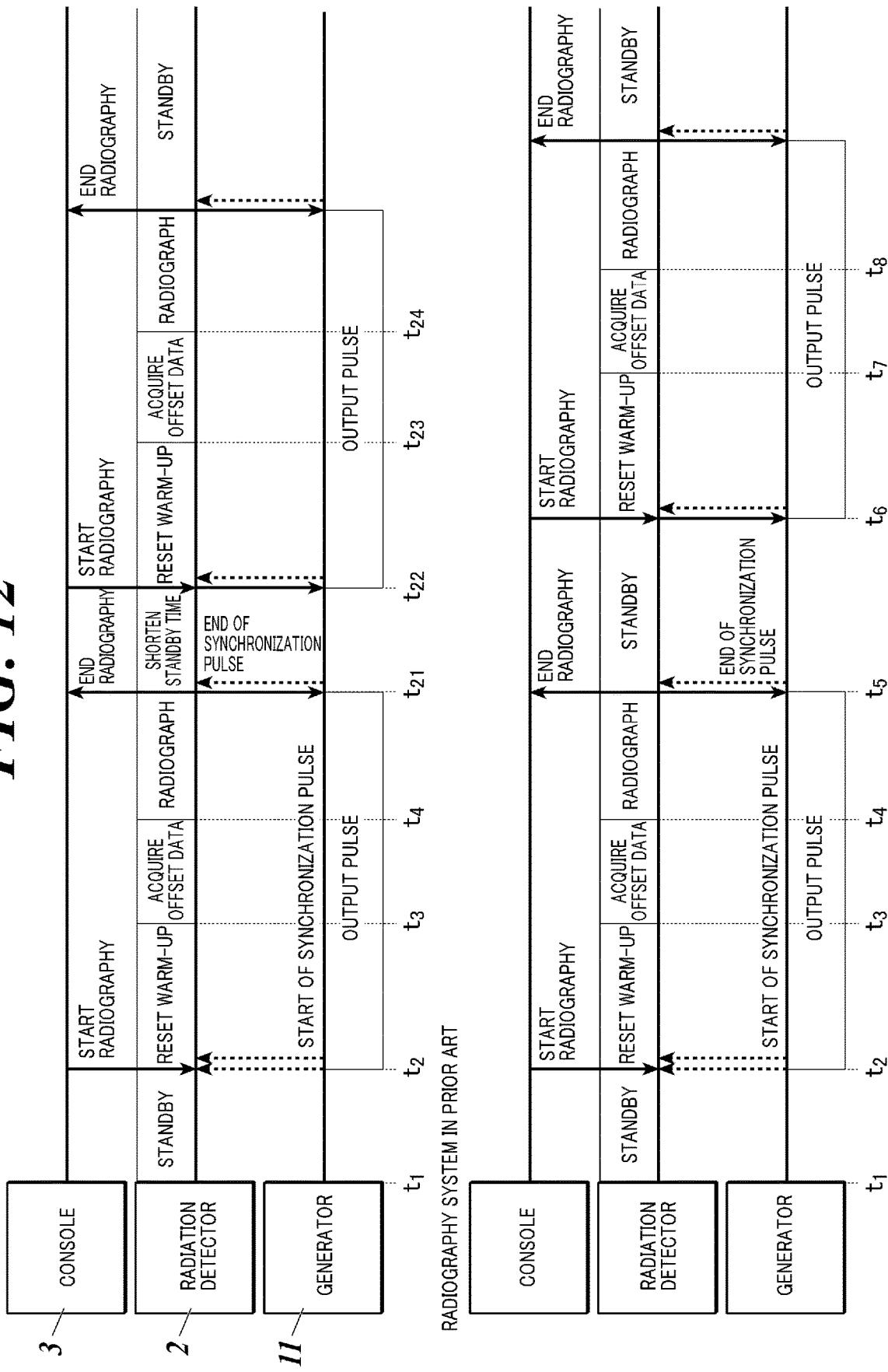
FIG. 12 is a timing chart showing operation of the radiography system according to the second embodiment.

FIG. 12 is a timing chart showing operation of the system 100A and operation of a conventional radiography system.

As shown in the upper part of FIG. 12, when the radiation command switch 12 of the radiation device 1A is operated in the offset acquisition mode, the generator 11A switches the pulse width of the first timing signal to the first pulse width. On the other hand, the radiation detector 2A switches the operation mode to the shooting mode ($t_4$). Thereby serial radiography is performed.

If the next test action is the first serial radiography, the generator 11A stops the first timing signal after current serial radiography. On the other hand, the radiation detector 2A generates the second timing signal and switches the operation mode to the shorter standby time mode ($t_{21}$).

Then, the console 3 transmits the radiography start signal to the generator 11 and the radiation detector 2 of the radiation device 1 ($t_{22}$).

After the generator 11A receives the radiography start signal, the generator 11A resumes generation of the first timing signal. On the other hand, the radiation detector 2A switches the operation mode to the reset mode.

A standby time after switching to the reset mode, the radiation detector 2A switches the operation mode to the offset acquisition mode ($t_{23}$). The standby time is shorter than that in the reset mode before the last serial radiography.

In the offset acquisition mode, when the radiation command switch 12 of the radiation device 1A is operated, the generator 11A switches the pulse width of the first timing signal to the first pulse width. On the other hand, the radiation detector 2A switches the operation mode to the shooting mode ($t_{24}$). Thereby the next serial radiography is performed.

According to the conventional radiography system, it is necessary to go through the standby mode, the reset mode for a predetermined time, and the offset acquisition mode between end of serial radiography and start of the next serial radiography. However, the system 100A switches the operation mode to the shorter standby time mode (the standby mode with the reset operation) after serial radiography ($t_{21}$). It shortens time of the next reset mode.

The standby time before the next shooting is shortened by a difference between:
 a time between $t_6$ and $t_7$; and
 a time between $t_{22}$ and $t_{23}$ in FIG. 8.

2-5. Advantageous Effect

As described above, after or during serial radiography by the radiation detector 2A, the system 100A according to the embodiment determines that the next test action is the first serial radiography which has the same frame rate as that in the last or current radiography. Then, before the next test action begins, the system 100A makes the radiation detector 2A turn the switch element on/off like it does in serial radiography (the system 100A switches the operation mode to the shorter standby time mode).

Like the system 100 according to the first embodiment, according to the system 100A, when serial radiography is followed by the next serial radiography, the standby time between shooting actions is shortened without degrading quality of video acquired in the next serial radiography.

Like the system 100 according to the first embodiment, in the case where additional radiography is performed after failure in one serial radiography, a length of the standby time is not so long as that in the case where serial radiography is newly performed.

3. Miscellaneous

The present invention is described above based on the embodiments. The present invention is not limited to the above embodiments and can be modified within scope of the claims of the present invention.

In the above examples, a hard disk, semiconducting non-volatile memory, or the like is used as a computer-readable medium storing the program according to the present invention. The present invention is not limited to those examples. A portable recording medium such as CD-ROM may also be applied as the computer-readable medium. A carrier wave may also be applied as a medium that provides data of the program according to the present invention via a communication line.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese patent application No. 2020-114532, filed on Jul. 2, 2020, is incorporated herein by reference in its entirety.

What is claimed is:

1. A radiography system, comprising:
an image former that performs serial radiography of repeatedly generating a frame that constitutes a video;
a first determiner that determines whether a next test action is the serial radiography or a first serial radiography that has a same frame rate as the serial radiography; and
an operation controller, wherein in a case where the first determiner determines that the next test action is the serial radiography or the first serial radiography, the operation controller switches the operation mode of the image former to a shorter standby time mode in which the operation controller stops drive of a reader included in the image former, and makes the image former turn a switch element on/off in a same manner as a manner in the serial radiography before start of the next test action.

2. The radiography system according to claim 1, wherein, after or during the serial radiography by the image former, the first determiner determines whether the next test action is the first serial radiography.

3. The radiography system according to claim 1, further comprising:
a first signal generator that repeatedly generates a first timing signal at a set cycle; and
a second signal generator that repeatedly generates a second timing signal at a set cycle,
wherein
while the first signal generator generates the first timing signal, the image former repeatedly turns the switch element on/off or repeatedly generates a frame based on the first timing signal,
while the first signal generator does not generate the first timing signal, the image former repeatedly turns the switch element on/off based on the second timing signal, and
the image former applies offset correction to the generated frame based on pieces of offset data, the number of pieces corresponding to a level of difference between the first timing signal and the second timing signal.

4. The radiography system according to claim 1, further comprising:
a console that sets various shooting conditions on the image former,
wherein the first determiner determines whether a next test action is the serial radiography based on contents of the next test action received from the console.

5. The radiography system according to claim 1 wherein in a case where the first determiner determines that the next test action is not the first serial radiography, the operation controller switches an operation mode of the image former to a standby mode in which the operation controller stops drive of a reader included in the image former and stops the image former from turning on/off the switch element.

6. A radiography system, comprising:
an image former that performs serial radiography of repeatedly generating a frame that constitutes a video;
a first determiner that determines whether a next test action is a first serial radiography that has a same frame rate as the serial radiography after or during the serial radiography by the image former; and
an operation controller,
wherein,
in a case where the first determiner determines that the next test action is not the first serial radiography, the operation controller switches an operation mode of the image former to a standby mode in which the operation controller stops drive of a reader included in the image former and stops the image former from turning on/off the switch element,
in a case where the first determiner determines that the next test action is the first serial radiography, the operation controller switches the operation mode of the image former to:
a shorter standby time mode in which the operation controller stops drive of the reader, and makes the image former turn the switch element on/off; or
an offset acquisition mode in which the operation controller drives the reader in a same manner as a manner in generation of a frame, and makes the image former turn the switch element on/off.

7. The radiography system according to claim 6, wherein, a predetermined standby time after switching to the shorter standby time mode, the operation controller switches the operation mode to the offset acquisition mode.

8. The radiography system according to claim 6, further comprising:
a second determiner that determines whether a cable is to be connected to the image former in the next test action,
wherein, in a case where the second determiner determines that the cable is not to be connected to the image former in the next test action, the operation controller switches the operation mode of the image former to the standby mode whatever a result of determination by the first determiner is.

9. The radiography system according to claim 8, wherein in the case where the first determiner determines that the next test action is not the first serial radiography, the first determiner further determines whether the next test action is a second serial radiography that has a frame rate different from the frame rate in the last or current radiography, and
the radiography system further comprises a notification controller that notifies a notification unit of how long a standby time before start of the next serial radiography is in the case where the determiner determines that the next test action is the first serial radiography and in the case where the determiner determines that the next test action is the second serial radiography.

10. The radiography system according to claim 9, further comprising:
a time setting unit that sets the standby time according to a part to be imaged in next shooting.

11. The radiography system according to claim 6, further comprising:
- a first signal generator that repeatedly generates a first timing signal of two types at a same timing and at a set cycle, the two types consisting of a first type that orders radiation and a second type that does not order radiation; and
- a third determiner that determines whether the first timing signal generated by the first signal generator is of the first type,
- wherein, in a case where the third determiner determines that the first timing signal of the first type has changed to the first timing signal of the second type, the operation controller changes operation mode of the image former not to the standby mode but to a shorter standby time mode.

12. The radiography system according to claim 11, further comprising:
- a measurer that measures temperature of the image former;
- an acquisition unit that, in a case where the temperature of the image former exceeds a predetermined threshold value, acquires a missing map based on pieces of offset data that are acquired while the operation mode of the image former is the offset acquisition mode, the missing map corresponding to the temperature measured by the measurer;
- a storage that stores the missing map acquired by the acquisition unit; and
- an update unit that replaces one missing map stored in the storage with another missing map acquired by the acquisition unit.

13. The radiography system according to claim 6, wherein in a case where the first determiner determines that the next test action is the first serial radiography, the operation controller switches the operation mode of the image former to a shorter standby time mode in which the operation controller stops drive of the reader, and makes the image former turn the switch element on/off.

14. The radiography system according to claim 6, wherein in a case where the first determiner determines that the next test action is the first serial radiography, the operation controller switches an operation mode of the image former to an offset acquisition mode in which the operation controller drives the reader in a same manner as a manner in generation of a frame, and makes the image former turn the switch element on/off.

* * * * *